(12) United States Patent
Liu et al.

(10) Patent No.: US 12,247,944 B2
(45) Date of Patent: Mar. 11, 2025

(54) GAS SENSOR AND PROTECTION MEMBER FOR GAS SENSOR

(71) Applicant: NGK SPARK PLUG CO., LTD., Nagoya (JP)

(72) Inventors: Sunchao Liu, Nagoya (JP); Kazuhiro Kouzaki, Nagoya (JP); Takehiro Oba, Nagoya (JP); Motohiko Nakamura, Nagoya (JP); Kenji Masuda, Nagoya (JP)

(73) Assignee: NITERRA CO., LTD., Nagoya (JP)

( * ) Notice: Subject to any disclaimer, the term of this patent is extended or adjusted under 35 U.S.C. 154(b) by 31 days.

(21) Appl. No.: 17/769,575

(22) PCT Filed: Sep. 28, 2020

(86) PCT No.: PCT/JP2020/036572
§ 371 (c)(1),
(2) Date: Apr. 15, 2022

(87) PCT Pub. No.: WO2021/199462
PCT Pub. Date: Oct. 7, 2021

(65) Prior Publication Data
US 2024/0125731 A1   Apr. 18, 2024

(30) Foreign Application Priority Data

Mar. 30, 2020  (JP) .................. 2020-060446

(51) Int. Cl.
*G01N 27/407* (2006.01)
*G01N 33/00* (2006.01)
(52) U.S. Cl.
CPC ..... *G01N 27/4077* (2013.01); *G01N 33/0027* (2013.01)

(58) Field of Classification Search
None
See application file for complete search history.

(56) References Cited

FOREIGN PATENT DOCUMENTS

| JP | 2004-245663 A | 9/2004 |
|---|---|---|
| JP | 2016-211981 A | 12/2016 |

OTHER PUBLICATIONS

English translation of JP 2004245663 (Year: 2004).*
International Search Report for PCT/JP2020/036572 dated Oct. 27, 2020 (PCT/ISA/210).

* cited by examiner

*Primary Examiner* — J. Christopher Ball
(74) *Attorney, Agent, or Firm* — Sughrue Mion, PLLC (57) ABSTRACT

A gas sensor (1) including a sensor element (10); a metallic shell (138); a tubular outer surface member (190) attached directly or indirectly to the metallic shell, constitutes an outer surface of the gas sensor, and extends toward a rear end side in relation to the metallic shell; and a tubular protection member (210, 220) which is detachably fixed to a fixation region C1, C2 of an outer circumference of the outer surface member. The protection member includes a first arc portion (212), a second arc portion (222), and a fixation portion (214,224) brought into contact with and is fixed to the fixation region. When the protection member fixed to the outer circumference of the outer surface member by fixing the fixation portion to the fixation region is viewed in the axial O direction, the first arc portion and the second arc portion cover in total at least 90% of the entire circumference of the outer surface of the outer surface member.

10 Claims, 8 Drawing Sheets

GAS SENSOR AND PROTECTION MEMBER FOR GAS SENSOR

CROSS-REFERENCE TO RELATED APPLICATIONS

The application is a National Stage of International Application No. PCT/JP2020/036572 filed Sep. 28, 2020, claiming priority based on Japanese Patent Application No. 2020-060446 filed Mar. 30, 2020, the above-noted applications incorporated herein by reference in their entirety.

BACKGROUND OF THE INVENTION

1, Field of the Invention

The present invention relates to a gas sensor including a sensor element which is exposed to a subject gas and detects a specific gas component in the subject gas, and to a protection member for the gas sensor.

2. Description of Related Art

An air-fuel ratio sensor and an oxygen sensor for detecting the concentration of oxygen in exhaust gas have been known as gas sensors used for improving the fuel efficiency of an internal combustion engine such as an automotive engine and for performing combustion control therefor.

In a structure generally used for such a gas sensor, a sensor element for detecting the concentration of a specific gas is held in a metallic shell, and a rear-end-side portion of the sensor element is accommodated in a metallic outer casing. A detection cell of the sensor element includes a reference electrode exposed to outside air used as a reference of oxygen concentration, and a detection electrode exposed to a subject gas. Therefore, the outside air must be introduced to the sensor element accommodated in the outer casing.

A gas sensor designed in consideration of the above is disclosed (see, for example, Patent Document 1). In the disclosed gas sensor, ventilation holes are formed in the side wall of a portion of the outer casing facing a separator, and a water-repellent filter is disposed to cover the ventilation holes.

In this gas sensor, a protection outer casing is further disposed on the outer side of the filter, and ventilation holes are also formed in the side wall of the protection outer casing. Therefore, the outside air is introduced into the interior of the outer casing through the ventilation holes and the filter.

Incidentally, the protection outer casing and its ventilation holes are exposed to the outside. Therefore, if, for example, high pressure water used for washing an automobile directly strikes the filter through the ventilation holes and the pressure of the water is higher than the withstanding water pressure of the filter, water invades the sensor element. This may cause a decrease in the detection accuracy of the sensor or a malfunction.

A conceivable measure is to cover the sensor element with a protection cover. For example, a technique of using, as a heat shield, an annular metallic cover having a slit; i.e., a C-like cross section, is disclosed (see, for example, Patent Document 2).

By virtue of this technique, the metallic cover can be easily and detachably attached to a gas sensor installed in an automobile or the like and having lead wires by attaching the cover while inserting the lead wires into the gap of the cover.

Patent Document 1: Japanese Patent Application Laid-Open (kokai) No. 2016-211981 (FIG. 1)
Patent Document 2: Japanese Patent Application Laid-Open (kokai) No. 2004-245663

3. Problems to be Solved by the Invention

In the case of the technique disclosed in Patent Document 2, since it is necessary to pass the lead wires through the gap of the metallic over, the metallic cover is attached to the gas sensor while widening the gap by expanding the cover. If the metallic cover is expanded excessively, the cover plastically deforms, which leads to a decrease in the force of attachment to the gas sensor and/or deformation of the cover. Therefore, the operation of attaching the cover must be performed carefully.

SUMMARY OF THE INVENTION

The present invention has been accomplished in view of the above problems of the related art, and an object of the present invention is to provide a gas sensor which includes a protection member which can be easily and detachably fixed to the circumference of the gas sensor without deforming the protection member and which can prevent foreign objects from directly striking the gas sensor. Another object of the present invention is to provide a protection member for the gas sensor.

The above objects have been achieved by providing, in a first aspect (1) of the invention, a gas sensor comprising a sensor element extending in an axial direction; a metallic shell which surrounds a circumference of the sensor element and holds the sensor element; a tubular outer surface member which is attached directly or indirectly to the metallic shell, constitutes an outer surface of the gas sensor, and extends toward a rear end side in relation to the metallic shell; and a tubular protection member which is detachably fixed to a fixation region of an outer circumference of the outer surface member. The gas sensor is characterized in that the protection member includes a first arc portion, a second arc portion, and a fixation portion which is brought into contact with and is fixed to the fixation region; and when the protection member fixed to the outer circumference of the outer surface member by fixing the fixation portion to the fixation region is viewed in the axial direction, the first arc portion and the second arc portion cover in total at least 90% of the entire circumference of the outer surface of the outer surface member.

In the above gas sensor (1), the protection member has a first arc portion and a second arc portion. Therefore, at least 90% (in total) of the outer surface of the outer surface member can be covered by fixing the protection member to the outer surface member via the fixation portion so that the first arc portion and the second arc portion meet each other.

As a result, it is possible to cover the outer surface of the outer surface member without fail, thereby preventing a foreign object from directly striking the gas sensor. Also, since the only requirement is to attach the protection member to the outer surface of the outer surface member so that the first arc portion and the second arc portion meet each other, it is unnecessary to forcedly expand a single arc portion, and the protection member can be easily and detachably fixed without deforming the protection member.

In the case where the protection member is damaged by a flying pebble, the protection member can be easily detached from the gas sensor.

In a preferred embodiment (2) of the gas sensor (1), the protection member is composed of two members which have the first arc portion and the second arc portion, respectively, and individual fixation portions connected to the first arc portion and the second arc portion, respectively, and the first arc portion and the second arc portion can be separated from each other.

In the above gas sensor, the protection member can be easily and detachably fixed to the gas sensor without deforming the protection member.

In another preferred embodiment (3) of the gas sensor (1), the first arc portion and the second arc portion of the protection member are connected by means of a connection portion, and the spacing between the first arc portion and the second arc portion in a radial direction can be expanded and contracted by rotation of opposite halves of the connection portion in the radial direction.

In the above gas sensor, the protection member can be easily and detachably fixed to the gas sensor without deforming the protection member.

In yet another preferred embodiment (4) of any of gas sensors (1) to (3), when the protection member fixed to the outer circumference of the outer surface member is viewed in the axial direction, the first arc portion and the second arc portion may cover the entire circumference of the outer surface of the outer surface member.

In the above gas sensor, the entire circumference (100%) of the outer surface of the outer surface member is covered without forming a gap. As a result, the effect of protecting the outer surface member can be obtained without fail.

In yet another preferred embodiment (5) of any of the gas sensors (1) to (4), the outer surface of the outer surface member has a diameter-reduced portion recessed inward in the radial direction and serving as the fixation region; and the fixation portion is fitted onto the diameter-reduced portion, thereby being fixed to the diameter-reduced portion.

In the above gas sensor, the protection member is fixed by utilizing the diameter-reduced portion provided on the outer surface member.

In yet another preferred embodiment (6) of any of the gas sensors (1) to (5), the outer surface member has a ventilation hole for introducing outside air into a space inside the outer surface member; an air-permeable filter is disposed on an inner surface of the outer surface member to close the ventilation hole; and the first arc portion and the second arc portion cover the ventilation hole from a radially outer side and form gaps for establishing communication between the ventilation hole and an outside atmosphere, the gaps being located at positions different from that of the ventilation hole in the axial direction.

In the above gas sensor, the first arc portion and the second arc portion establish communication between the ventilation hole and the outside atmosphere through the gap G without closing the ventilation hole.

In yet another preferred embodiment (7) of any of the gas sensors (1) to (6), the total sum of a center angle of the first arc portion and a center angle of the second arc portion is greater than 360 degrees.

In the above gas sensor, since the first arc portion and the second arc portion overlap each other in the circumferential direction, the entire circumference (100%) of the outer surface of the outer surface member is covered without forming a gap. As a result, the effect of protecting the outer surface member can be obtained without fail.

In a preferred embodiment (8) of the gas sensor (7), a diameter of the first arc portion and a diameter of the second arc portion are the same; one end portion of the first arc portion in a circumferential direction covers the outer surface of the outer surface member, and the other end portion of the first arc portion covers one end portion of the second arc portion in the circumferential direction; and the one end portion of the second arc portion in the circumferential direction covers the outer surface of the outer surface member, and the other end portion of the second arc portion covers the one end portion of the first arc portion in the circumferential direction.

In the above gas sensor, opposite ends of the first arc portion are staggered in relation to opposite ends of the second arc portion and overlap with the opposite ends of the second arc portion. Therefore, when the first arc portion and the second arc portion overlap with each other, the opposite ends of the first arc portion do not interfere with the opposite ends of the second arc portion, and the assembly operation becomes easy. Also, since the opposite ends of the first arc portion overlap with the opposite ends of the second arc portion, the entire circumference (100%) of the outer surface of the outer surface member is covered without forming a gap. As a result, the effect of protecting the outer surface member can be obtained without fail.

In another preferred embodiment (9) of any of the gas sensors (7) and (8), a diameter of the first arc portion is greater than a diameter of the second arc portion; the first arc portion has a center angle greater than 180 degrees; and end portions of the second arc portion on opposite sides in the circumferential direction are covered by the first arc portion.

In the above gas sensor, when the first arc portion and the second arc portion overlap with each other, the opposite ends of the first arc portion do not interfere with the opposite ends of the second arc portion, and the assembly operation becomes easy.

In another preferred embodiment (10) of any of the gas sensors (1) to (7), the fixation portion has elasticity; when viewed in the axial direction, the fixation portion has the shape of an arc having a center angle greater than 180 degrees and an opening; the minimum spacing of the opening in the circumferential direction is smaller than the outer diameter of the fixation region; and the fixation portion has guide portions located at opposite ends of the opening, and the spacing between the guide portions in the circumferential direction expands from the minimum spacing.

In the above gas sensor, when the guide portions are pressed against a portion of the outer surface member to which the fixation portion is to be fixed, the guide portions move along the outer surface of that portion and expand in the radial direction. Therefore, the guide portions serve as guides when the fixation portion is fitted onto that portion to which the fixation portion is to be fixed.

In a second aspect (11), the invention provides a protection member for a gas sensor including a sensor element extending in an axial direction, a metallic shell surrounding a circumference of the sensor element and holding the sensor element, and a tubular outer surface member attached directly or indirectly to the metallic shell, constituting an outer surface of the sensor element, and extending toward a rear end side in relation to the metallic shell. The protection member is characterized in that the protection member is detachably fixed to a fixation region of an outer circumference of the outer surface member; the protection member includes a first arc portion, a second arc portion, and a fixation portion which is brought into contact with and is fixed to the outer surface member; and when the protection member fixed to the outer circumference of the outer surface member by fixing the fixation portion to the outer surface member is viewed in the axial direction, the first arc portion and the second arc portion cover in total at least 90% of the entire circumference of the outer surface of the outer surface member.

Effects of the Invention

According to the present invention, the protection member can be easily and detachably fixed to the circumference of the gas sensor without deforming the protection member, and can prevent foreign objects from directly striking the gas sensor.

DESCRIPTION OF REFERENCE NUMERALS

Reference numerals used to identify various features in the drawings include the following.
1B: gas sensor
10: sensor element
138: metallic shell
144: outer casing
144$h$: first ventilation hole
180: filter
190: outer surface member (protection outer casing)
190$h$: ventilation hole (second ventilation hole)
210-250: protection member
212, 232, 252, 262: first arc portion
222, 242, 256, 272: second arc portion
214, 224, 234, 244, 254, 258: fixation portion
214$a$, 214$b$, 224$a$, 224$b$, 234$a$, 234$b$, 244$a$, 244$b$, 244$a$, 258$a$: guide portion
232$e$1: one end portion of the first arc portion
232$e$2: other end portion of the first arc portion
242$e$1: other end portion of the second arc portion
242$e$2: one end portion of the second arc portion
259: connection portion
O: axial line
C1, C2: fixation region, diameter-reduced portion (crimped portion)
W1: fixation region (weld portion)
R1: outer surface member (region of the outer casing not covered by the protection outer casing)
G: gap
$\theta$1: center angle of the fixation portion
$\theta$2: center angle of the arc portion

DETAILED DESCRIPTION OF THE PREFERRED EMBODIMENTS

Embodiments of the present invention will next be described in greater detail with reference to the drawings. However, the present invention should not be construed as being limited thereto.

Figure 1:
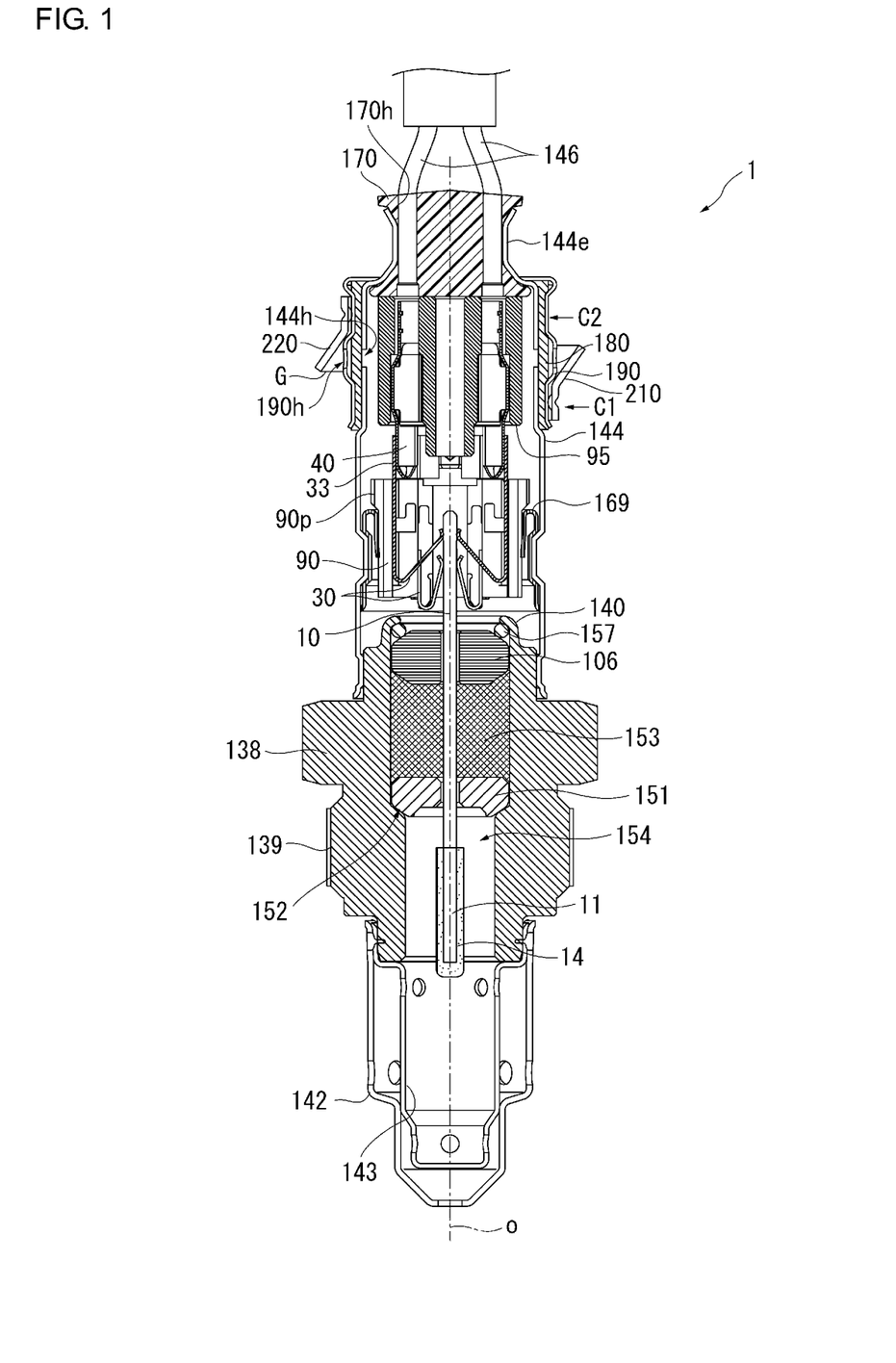
FIG. 1 is a sectional view of a gas sensor according to a first embodiment of the present invention along an axial direction.
Figure 2:
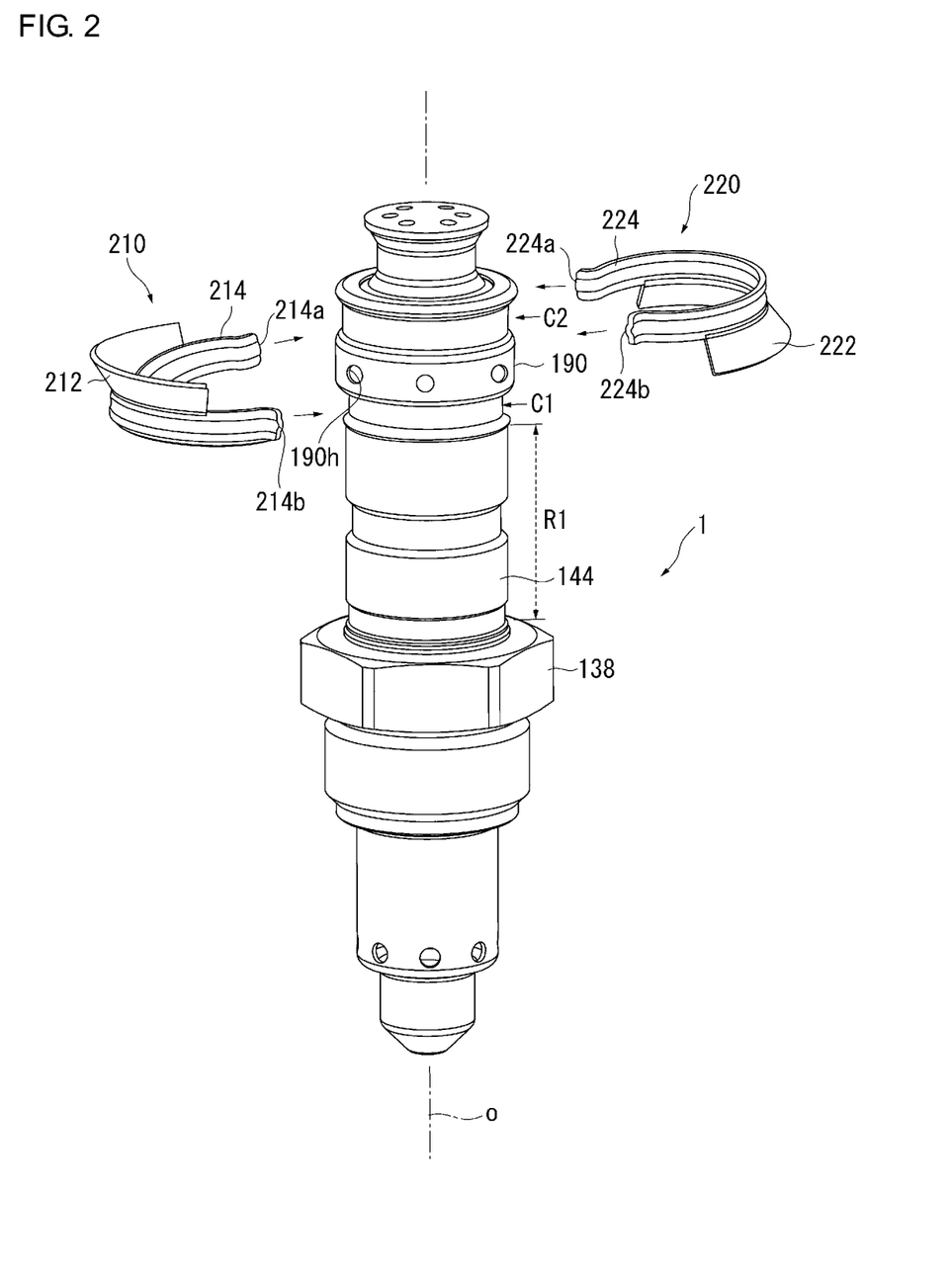
FIG. 2 is an exploded perspective view of protection portions.
Figure 3:
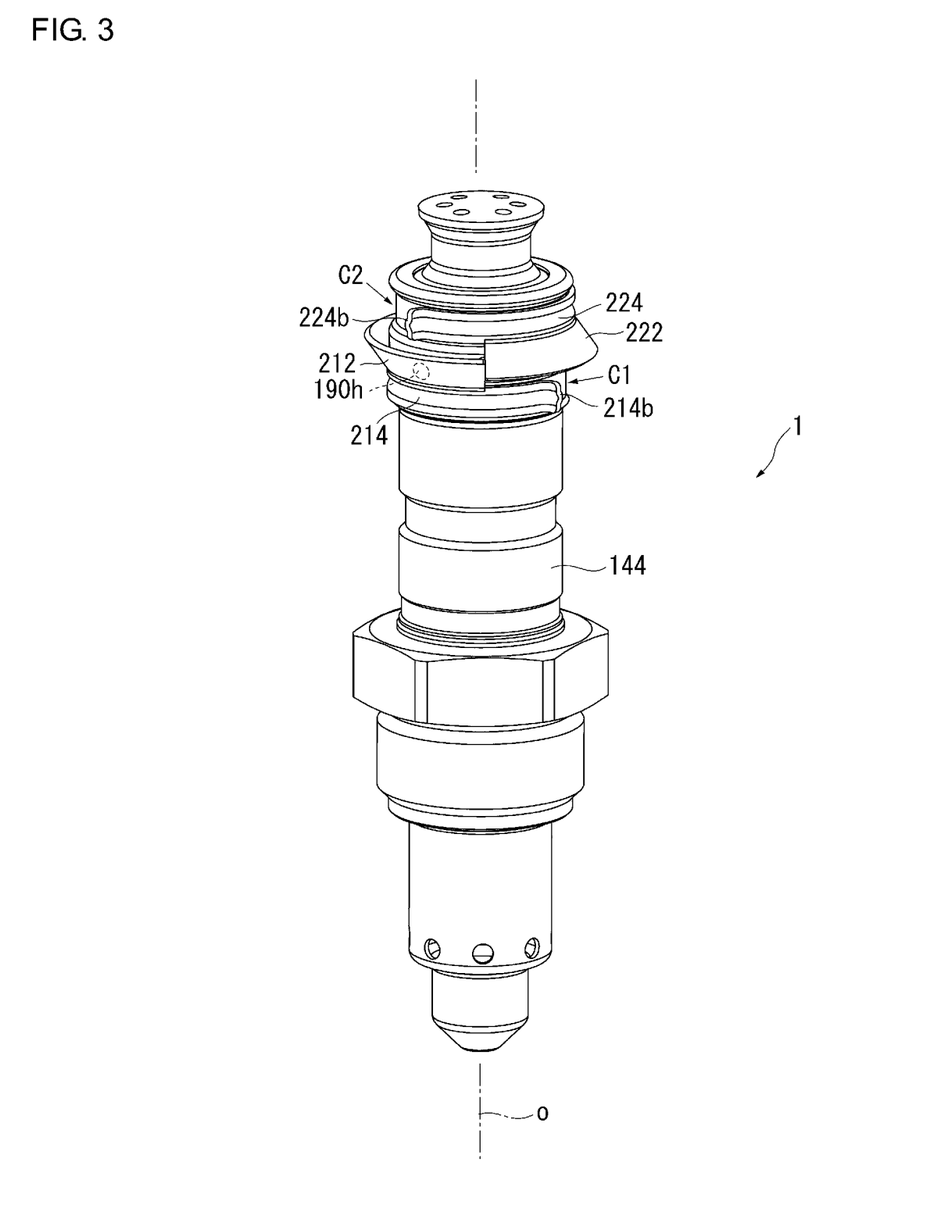
FIG. 3 is a perspective view of the gas sensor with the protection portions fixed thereto.
Figure 4:
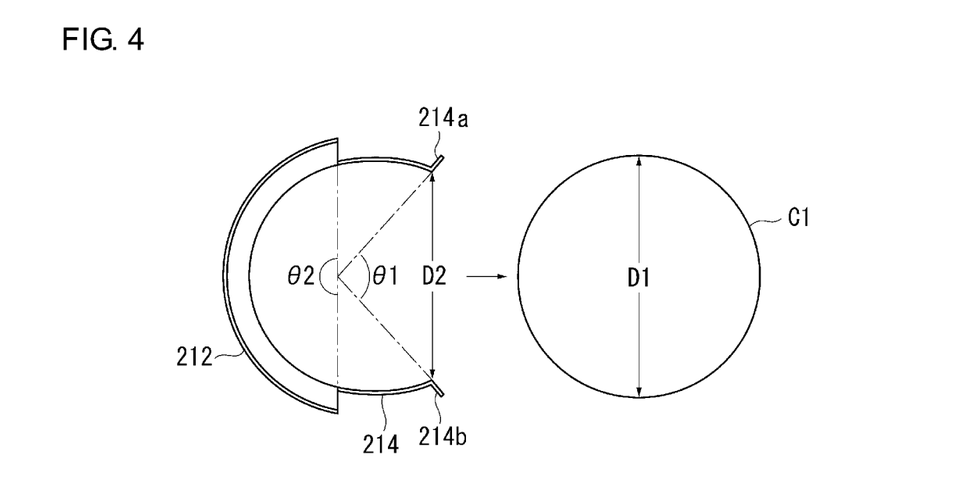
FIG. 4 is a sectional view showing a method for fixing a protection portion to a crimped portion.
Figure 5:
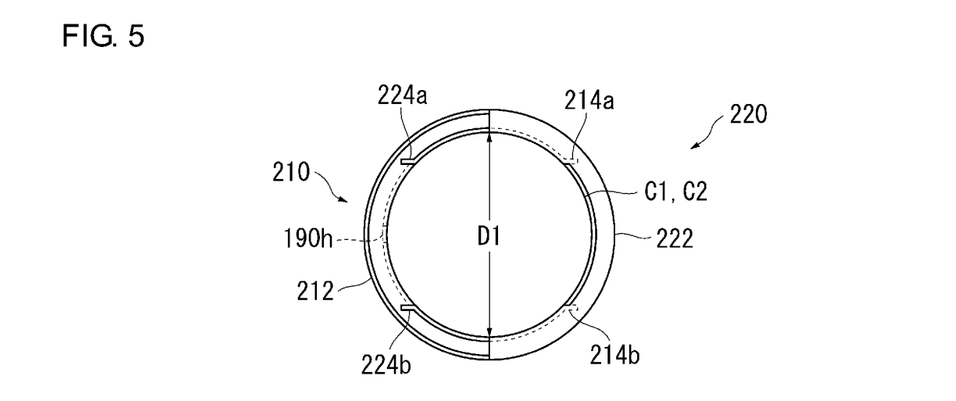
FIG. 5 is a sectional view showing a state in which the protection portions have been fixed to the crimped portions.

FIG. 1 is an overall sectional view of a gas sensor (oxygen sensor) 1 according to a first embodiment of the present invention taken along the direction of an axial line O. FIG. 2 is an exploded perspective view of protection portions 210 and 220. FIG. 3 is a perspective view of the gas sensor 1 with the protection portions 210 and 220 fixed thereto. FIG. 4 is a sectional view showing a method for fixing the protection portion 210 to a crimped portion C1. FIG. 5 is a sectional view showing a state in which the protection portions 210 and 220 have been fixed to the crimped portions C1 and C2.

Notably, FIGS. 4 and 5 are sectional views taken perpendicular to the axis line O in FIG. 3 (namely, as viewed from the rear end side of the crimped portion C2 toward the forward end side).

The gas sensor 1 is an oxygen sensor for detecting the concentration of oxygen in exhaust gas from automobiles and various internal combustion engines.

In FIG. 1, the gas sensor 1 includes a tubular metallic shell 138 having a screw portion 139 formed on its outer surface and used for fixing the gas sensor 1 to an exhaust pipe; a plate-shaped sensor element 10 extending in the direction of the axial line O (the longitudinal direction of the gas sensor 1: the vertical direction in the drawing); a tubular outer casing 144 attached to the metallic shell 138, extending toward the rear end side, and covering a rear end portion of the sensor element 10; a tubular protection outer casing 190 covering the outer casing 144; a filter 180 sandwiched and held between the outer casing 144 and the protection outer casing 190; two protection members 210 and 220, described below; and other members.

A plurality of electrode pads (not shown) are arranged on the opposite sides of a rear end portion of the sensor element 10. Meanwhile, a gas detection portion 11 at the forward end of the sensor element 10 is covered with a porous protection layer 14 formed of, for example, alumina.

The metallic shell 138 is an approximately tubular member formed of stainless steel and having a through hole 154 extending therethrough in the direction of the axial line and a ledge portion 152 protruding toward a radially inward region of the through hole 154. The sensor element 10 is disposed in the through hole 154 so that its forward end portion protrudes from the forward end of the through hole 154. The ledge portion 152 has an inward tapered surface inclined with respect to a plane perpendicular to the axial direction.

Notably, within the through hole 154 of the metallic shell 138, an approximately annular ceramic holder 151 formed of alumina, a powder filled layer 153 (hereinafter also referred to as a talc ring 153), and a ceramic sleeve 106 are stacked in this order from the forward end side to the rear end side so as to surround the circumference of the sensor element 10.

Also, a crimp packing 157 is disposed between the ceramic sleeve 106 and a rear end portion 140 of the metallic shell 138. The rear end portion 140 of the metallic shell 138 is crimped so as to press the ceramic sleeve 106 toward the forward end side through the crimp packing 157.

Meanwhile, as shown in FIG. 1, a dual protector formed of metal (e.g., stainless steel) is attached by, for example, welding to the outer circumference of a forward end portion (a lower portion in FIG. 1) of the metallic shell 138 and covers a protruding portion of the sensor element 10. The dual protector has a plurality of holes and is composed of an outer protector 142 and an inner protector 143.

An outer casing 144 is fixed to the outer circumference of a rear end portion of the metallic shell 138. Lead wires 146 are connected to rear end portions of respective rear-end-side metallic terminals 40 and extend toward the rear end side of a rear-end-side separator 95.

A grommet 170 formed of rubber is disposed in an opening of a rear end portion 144e (an upper end portion in FIG. 1) of the outer casing 144. The grommet 170 has lead wire insertion holes 170h into which six lead wires 146 (only two of them are illustrated in FIG. 1) extending from the rear-end-side separator 95 are inserted. The rear end portion 144e is crimped radially inward, whereby the grommet 170 is fixed inside the outer casing 144.

A forward-end-side separator 90 is disposed on the rear end side (the upper side in FIG. 1) of the sensor element 10 protruding from the rear end portion 140 of the metallic shell 138 and has a collar portion 90p protruding radially outward from the outer surface of the forward-end-side separator 90. The collar portion 90p abuts against the outer casing 144 through a holding member 169, and the forward-end-side separator 90 is thereby held within the outer casing 144.

The rear-end-side separator 95 is disposed between the grommet 170 and the forward-end-side separator 90, and elastic force of the grommet 170 causes the rear-end-side separator 95 to press the forward-end-side separator 90 toward the forward end side. As a result, the collar portion 90p is pressed against the holding member 169, and the forward-end-side separator 90 and the rear-end-side separator 95 are thereby held within the outer casing 144 in a mutually connected condition (i.e., without separation in the direction of the axial line O).

Four forward-end-side metallic terminals 30 are held in the forward-end-side separator 90, and the four rear-end-side metallic terminals 40 are held in the rear-end-side separator 95.

The forward-end-side metallic terminals 30 and the rear-end-side metallic terminals 40 are disposed on the forward end side and the rear end side, respectively, and the forward-end-side metallic terminals 30 are connected to the rear-end-side metallic terminals 40. Specifically, each forward-end-side metallic terminal 30 has a tubular portion 33 on the rear end side, and a tapered tube portion at the forward end of the corresponding rear-end-side metallic terminal 40 is inserted into the tubular portion 33.

The forward-end-side metallic terminals 30 are electrically connected to electrode pads disposed on the rear-end-side portion of the sensor element 10. A sensor output signal is outputted to the outside from the forward-end-side metallic terminals 30 and the rear-end-side metallic terminals 40 through the lead wires 146. Electric power is supplied to the heater section through the rear-end-side metallic terminals 40 and the forward-end-side metallic terminals 30.

Notably, the lead wires 146 are crimped to rear end portions of the rear-end-side metallic terminals 40, and the lead wires 146 extend to the outside through the lead wire insertion holes 170h of the grommet 170.

The sensor element 10 has a known structure. Although not illustrated, the sensor element 10 includes a gas detection section having an oxygen-ion permeable solid electrolyte body and a pair of electrodes; and a heater section for heating the gas detection section and maintaining the gas detection section at a constant temperature. The pair of electrodes of the gas detection section include a reference electrode exposed to outside air which serves as a reference for oxygen concentration, and a detection electrode exposed to a subject gas.

In order to introduce outside air to the sensor element 10 accommodated in the outer casing 144, a plurality of first ventilation holes 144h are formed in the side wall of the outer casing 144 at equal intervals in the circumferential direction. Also, an air-permeable filter 180 formed of resin is disposed on the radially outer side of the outer casing 144 so as to close the first ventilation holes 144h. Further, the protection outer casing 190 formed of metal is fitted onto the filter 180 so as to surround the filter 180 from the radially outer side.

The protection outer casing 190 has second ventilation holes 190h which overlap the first ventilation holes 144h, with the filter 180 intervening therebetween. Outside air can be introduced into the interior of the gas sensor 1 through the ventilation holes 144h and 190h and the filter 180, and the outside air can be discharged from the interior of the gas sensor 1 through the ventilation holes 144h and 190h and the filter 180.

The filter 180, which is water-repellent, allows air to pass therethrough but prevents invasion of moisture.

The protection outer casing 190 has crimped portions C1 and C2 crimped from the outer side toward the radially inner side in a state in which the filter 180 is sandwiched between the protection outer casing 190 and the outer casing 144, whereby the outer casing 144, the filter 180, and the protection outer casing 190 are integrally fixed.

In the present embodiment, the protection outer casing 190 has two crimped portions; i.e., the crimped portion C1 located on the forward end side of the first ventilation holes 144h and the second ventilation holes 190h, and the crimped portion C2 located on the rear end side of the first ventilation holes 144h and the second ventilation holes 190h.

The crimped portions C1 and C2 serve as diameter-reduced portions recessed radially inward from the outer surface of the circumference of the protection outer casing 190.

Next, the protection members 210 and 220, which are a characteristic feature of the present invention, will be described.

As shown in FIG. 2, the protection members are two separable members; i.e., the first protection member 210 having a first arc portion 212, and the second protection member 220 having a second arc portion 222. Each of the protection members 210 and 220 is formed of a metal plate and can elastically deform in the radial direction.

Specifically, the first protection member 210 has the first arc portion 212 which has an approximately semi-circular shape as viewed in the direction of the axial line O and is tapered such that its radius increases toward the rear end side, and a fixation portion 214 which is integrally connected to an end of the first arc portion 212 on the forward end side and has a larger center angle than the first arc portion 212. The fixation portion 214 has a C-like shape as viewed in the axial direction and has guide portions 214a and 214b located at opposite ends of its opening so that the spacing between the guide portions 214a and 214b increases toward the outer side in the circumferential direction.

The second protection member 220 is obtained by inverting the first protection member 210 in the radial direction and further inverting the first protection member 210 in the direction of the axial line O, and the second protection member 220 has the same shape as the first protection member 210. Accordingly, like the first protection member 210, the second protection member 220 has the second arc portion 222 and a fixation portion 224 integrally formed. Also, the second protection member 220 has guide portions 224a and 224b at opposite ends of the opening of the fixation portion 224.

As shown in FIGS. 2 and 3, when the guide portions 214a and 214b of the fixation portion 214 of the first protection member 210 are pressed against the crimped portion C1 from the radially outer side, the fixation portion 214 elastically expands in the radial direction and enters a groove defined by the crimped portion C1. As a result, the fixation portion 214 is fitted onto and fixed to the crimped portion C1 so that the fixation portion 214 presses the outer circumferential surface of the crimped portion C1.

Namely, as shown in FIG. 4, in the present embodiment, the fixation portion 214 of the first protection member 210 is configured so that the center angle θ1 is greater than 180 degrees, the minimum spacing D2 of the opening in the circumferential direction is smaller than the outer diameter D1 of the crimped portion C1, and the spacing between the guide portions 214a and 214b in the circumferential direction expands from the minimum spacing D2.

As a result, when the guide portions 214a and 214b are pressed against the crimped portion C1, the guide portions 214a and 214b move along the outer surface of the crimped portion C1 while expanding radially. Therefore, the guide portions 214a and 214b serve as guides when the fixation portion 214 is fitted onto the crimped portion C1.

Similarly, when the guide portions 224a and 224b of the fixation portion 224 of the second protection member 220 are pressed against the crimped portion C2 from the radially outer side, the fixation portion 224 elastically expands in the radial direction and enters a groove defined by the crimped portion C2. As a result, the fixation portion 224 is fitted onto and fixed to the crimped portion C2 so that the fixation portion 224 presses the outer circumferential surface of the crimped portion C2.

In this manner, the first protection member 210 and the second protection member 220 are attached so that, as shown in FIG. 5, the first arc portion 212 and the second arc portion 222 meet each other, as viewed in the direction of the axial line O, and cover at least 90% (in total) of the entire circumference of the outer surface of the protection outer casing 190.

Notably, in the present embodiment, the first arc portion 212 and the second arc portion 222 have the same shape and have a center angle θ2 (FIG. 4) of 180 degrees. As shown in FIG. 5, the opposite ends of the first arc portion 212 are in intimate contact with the opposite ends of the second arc portion 222, so that the entire circumference (100%) of the outer surface of the protection outer casing 190 is covered.

As described above, since the protection members 210 and 220 have the first arc portion 212 and the second arc portion 222, respectively, at least 90% (in total) of the outer surface of the protection outer casing 190 can be covered by fixing the protection members 210 and 220 to the crimped portions C1 and C2, respectively, so that the first arc portion 212 and the second arc portion 222 meet each other.

As a result, it is possible to cover the outer surface of the protection outer casing 190 without fail, thereby preventing foreign objects from directly striking the gas sensor 1. Also, since the only requirement is to attach the protection members 210 and 220 to the outer surface of the protection outer casing 190 so that the first arc portion 212 and the second arc portion 222 meet each other, it is unnecessary to forcedly expand a single arc portion, and the protection members 210 and 220 can be easily and detachably fixed without deforming the protection members 210 and 220.

In the case where the protection members 210 and 220 are damaged by a flying pebble or the like, the protection members 210 and 220 can be easily detached from the gas sensor 1.

Notably, rather than foreign objects striking the sensor element 10, the present embodiment prevents foreign objects from striking the main body of the gas sensor 1. Namely, in the present embodiment, the protection members 210 and 220 protect the protection outer casing 190, which is a constituent member of the gas sensor 1, and prevent foreign objects from directly striking the filter 180.

The crimped portions C1 and C2 correspond to the "fixation region" and the "diameter-reduced portion" of the invention.

The protection outer casing 190 corresponds to the "outer surface member" of the invention.

Notably, the "outer surface member" is a tubular member which is attached directly or indirectly to the metallic shell 138, constitutes an outer surface of the sensor element 10, and extends toward the rear end side in relation to the metallic shell 138. Namely, as shown in FIG. 2, a region R1 of the outer casing 144 attached directly to the metallic shell 138, which region is not covered by the protection outer casing 190, (namely, a region located between the protection outer casing 190 and the metallic shell 138 in the direction of the axial line O) also corresponds to the "outer surface member."

Also, as shown in FIG. 1, in the present embodiment, the first arc portion 212 and the second arc portion 222 cover the second ventilation holes 190h from the radially outer side and define respective gaps G at positions different from the position of the second ventilation holes 190h as viewed in the direction of the axial line O. The gaps establish communication between the second ventilation hole 190h and the outside atmosphere. Specifically, the gaps G are formed at the forward end edge of the first arc portion 212 and at the rear end edge of the second arc portion 222. Meanwhile, the first arc portion 212 and the second arc portion 222 overlap the second ventilation holes 190h in the direction of the axial line O and are spaced apart from the second ventilation holes 190h in the radial direction (FIG. 5).

By virtue of this configuration, the first arc portion 212 and the second arc portion 222 can establish communication between the second ventilation holes 190h and the outside atmosphere through the gaps G, without closing the second ventilation holes 190h.

The second ventilation holes 190h correspond to the "ventilation hole" of the invention.

Next, a gas sensor 1B according to a second embodiment of the present invention will be described with reference to FIGS. 6 to 8.

The gas sensor 1B according to the second embodiment of the present invention has the same structure as the gas sensor 1 according to the first embodiment, except that the gas sensor 1B includes protection portions 230 and 240 different from those of the gas sensor 1. Therefore, portions having the same structures as those of the gas sensor 1 are denoted by the same reference numerals, and their description will not be repeated.

Figure 6:
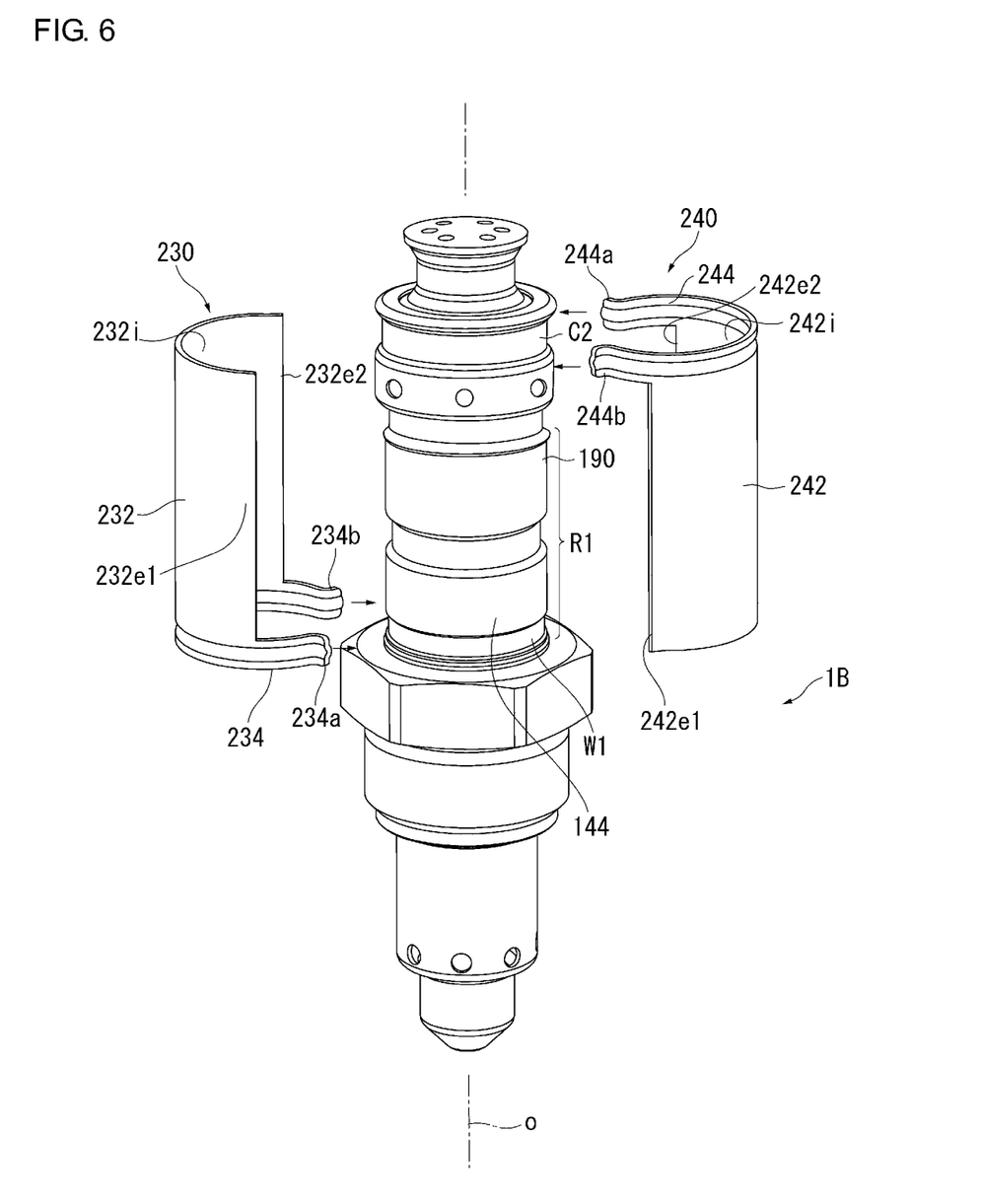
FIG. 6 is an exploded perspective view of protection portions in a gas sensor according to a second embodiment of the present invention.

FIG. 6 is an exploded perspective view of the protection portions 230 and 240 in the gas sensor (oxygen sensor) 1B according to the second embodiment of the present invention. FIG. 7 is a perspective view of the gas sensor 1B with the protection portions 230 and 240 fixed thereto. FIG. 8 is a sectional view showing a state in which the protection portions 230 and 240 have been fixed to the crimped portion C2 and a weld portion W1.

Figure 8:
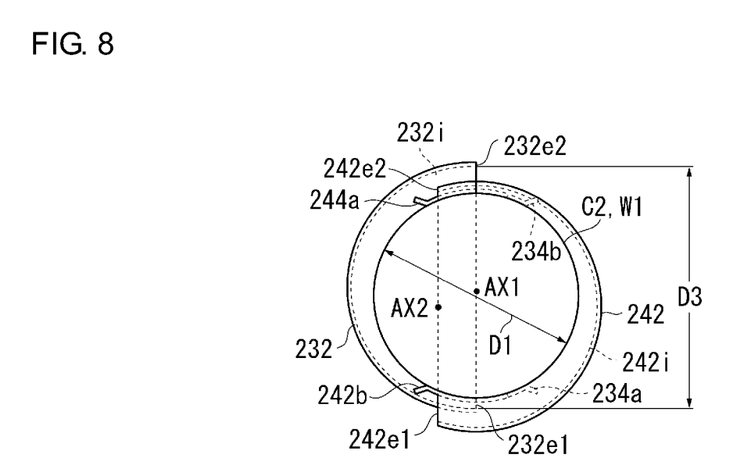
FIG. 8 is a sectional view showing a state in which the protection portions have been fixed to a crimped portion and a weld portion.

Notably, FIG. 8 is a sectional view as viewed from the rear end side of the crimped portion C2 toward the forward end side.

As shown in FIG. 6, the protection members are two separable members; i.e., the first protection member 230 having a first arc portion 232, and the second protection member 240 having a second arc portion 242. Each of the protection members 230 and 240 is formed of a metal plate and can elastically deform in the radial direction.

Specifically, the first protection member 230 has the first arc portion 232 which has an approximately semi-circular shape as viewed in the direction of the axial line O and straightly extends in the direction of the axial line O, and a fixation portion 234 which is integrally connected to an end of the first arc portion 232 on the forward end side and has a larger center angle than the first arc portion 232. The fixation portion 234 has a C-like shape as viewed in the axial direction and has guide portions 234*a* and 234*b* located at opposite ends of its opening so that the spacing between the guide portions 234*a* and 234*b* increases toward the outer side in the circumferential direction.

The second protection member 240 is obtained by inverting the first protection member 230 in the radial direction and further inverting the first protection member 230 in the direction of the axial line O, and the second protection member 240 has the same shape as the first protection member 230. Accordingly, like the first protection member 230, the second protection member 240 has the second arc portion 242 and an integrally fixation portion 244. Also, the second protection member 240 has guide portions 244*a* and 244*b* located at opposite ends of the opening of the fixation portion 244.

The forward end of the outer casing 144 forms a weld portion W1 attached to the circumference of the metallic shell 138 by means of welding performed along the entire circumference. The outer surface of the weld portion W1 forms a diameter-reduced portion which is recessed radially inward from the outer surface of the surrounding outer casing 144.

Figure 7:
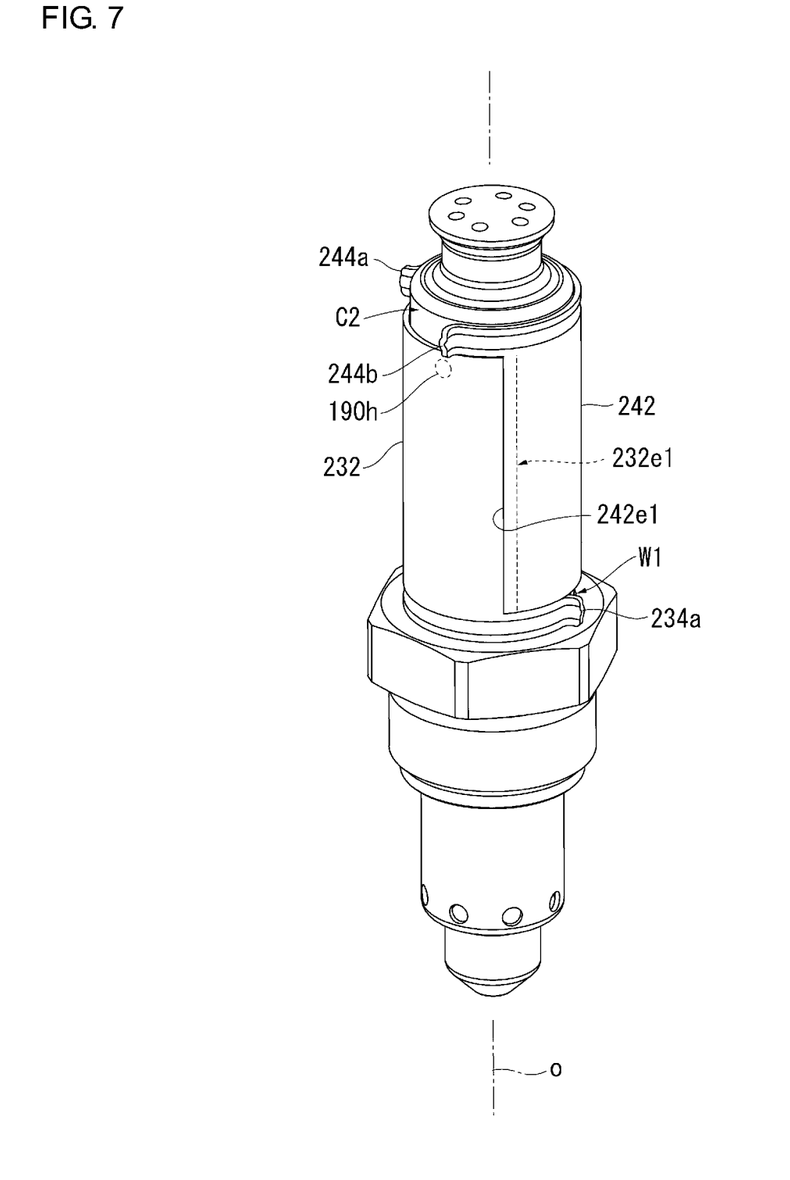
FIG. 7 is a perspective view of the gas sensor with the protection portions fixed thereto.

As shown in FIGS. 6 and 7, when the guide portions 234*a* and 234*b* of the fixation portion 234 of the first protection member 230 are pressed against the weld portion W1 from the radially outer side, the fixation portion 234 elastically expands in the radial direction and enters a groove defined by the weld portion W1. As a result, the fixation portion 234 is fitted onto and fixed to the weld portion W1 so that the fixation portion 234 presses the outer circumferential surface of the weld portion W1.

Similarly, when the guide portions 244*a* and 244*b* of the fixation portion 244 of the second protection member 240 are pressed against the crimped portion C2 from the radially outer side, the fixation portion 244 elastically expands in the radial direction and enters the groove defined by the crimped portion C2. As a result, the fixation portion 244 is fitted onto and fixed to the crimped portion C2 so that the fixation portion 244 presses the outer circumferential surface of the crimped portion C2.

In this manner, as shown in FIG. 7, the first arc portion 232 and the second arc portion 242 cover not only the outer surface of the protection outer casing 190, but also the outer surface of the region R1 of the outer casing 144.

In this manner, as shown in FIG. 8, the first arc portion 232 and the second arc portion 242 meet each other, as viewed in the direction of the axial line O, and cover at least 90% (in total) of the entire circumferences of the outer surface of the protection outer casing 190 and the outer surface of the region R1.

As a result, it is possible to cover the outer surface of the protection outer casing 190 and the outer surface of the region R1 without fail, thereby preventing foreign objects from directly striking the gas sensor 1. Also, since the only requirement is to attach the protection members 230 and 240 to the outer surface of the protection outer casing 190 and the outer surface of the region R1 so that the first arc portion 232 and the second arc portion 242 meet each other, it is unnecessary to forcedly expand a single arc portion, and the protection members 230 and 240 can be easily and detachably fixed without deforming the protection members 230 and 240.

Notably, in the present embodiment, the first arc portion 232 and the second arc portion 242 have the same shape and each has a center angle θ2 (corresponding to the center angle θ2 shown in FIG. 4) of 180 degrees. Meanwhile, each of the first arc portion 232 and the second arc portion 242 has an inner diameter D3 sufficiently larger than the outer diameter D1 of the protection outer casing 190 and the region R1.

By virtue of this configuration, as shown in FIG. 8, the first arc portion 232 and the second arc portion 242 can be disposed so that their axes AX1 and AX2 deviate from each other in the vertical direction of FIG. 8.

As a result, the opposite ends of the first arc portion 232 are staggered in relation to the opposite ends of the second arc portion 242 and are overlapped with opposite ends of the second arc portion 242. Specifically, one end portion 232*e*1 of the first arc portion 232 in the circumferential direction covers the outer surface of the outer surface member (the protection outer casing 190 and the region R1), and the other end portion 232*e*2 covers one end portion 242*e*2 of the second arc portion 242 in the circumferential direction. Also, one end portion 242*e*2 of the second arc portion 242 in the circumferential direction covers the outer surface of the outer surface member (the protection outer casing 190 and the region R1), and the other end portion 242*e*1 covers the one end portion 232*e*1 of the first arc portion 232 in the circumferential direction.

Notably, although the inner diameter D3 of the first arc portion 232 and the inner diameter D3 of the second arc portion 242 are "the same," "the same" allows a tolerance; for example, a difference of about ±0.1 mm.

Similarly, the first arc portion 212 and the second arc portion 222 of the first embodiment may have a dimensional difference therebetween. Reference numerals 232*i* and 242*i* in FIG. 8 represent the inner surfaces of the first arc portion 232 and the second arc portion 242, respectively.

As described above, opposite ends of the first arc portion 232 are staggered in relation to the opposite ends of the second arc portion 242 and are overlapped with the opposite ends of the second arc portion 242. Therefore, when the first arc portion 232 and the second arc portion 242 are overlapped with each other, the opposite ends of the first arc portion 232 do not interfere with opposite ends of the second arc portion 242, and the assembly operation becomes easy.

Also, since the opposite ends of the first arc portion 232 overlap with the opposite ends of the second arc portion 242, the entire circumference (100%) of the outer surface of the outer surface member (the protection outer casing 190 and the region R1) can be covered without forming a gap. As a result, the effect of protecting the outer surface member can be obtained without fail.

The weld portion W1 corresponds to the "fixation region" and the "diameter-reduced portion" of the invention.

Needless to say, the present invention is not limited to the above-described embodiments and encompasses various modifications and equivalents within the concept and scope of the invention.

Figure 9:
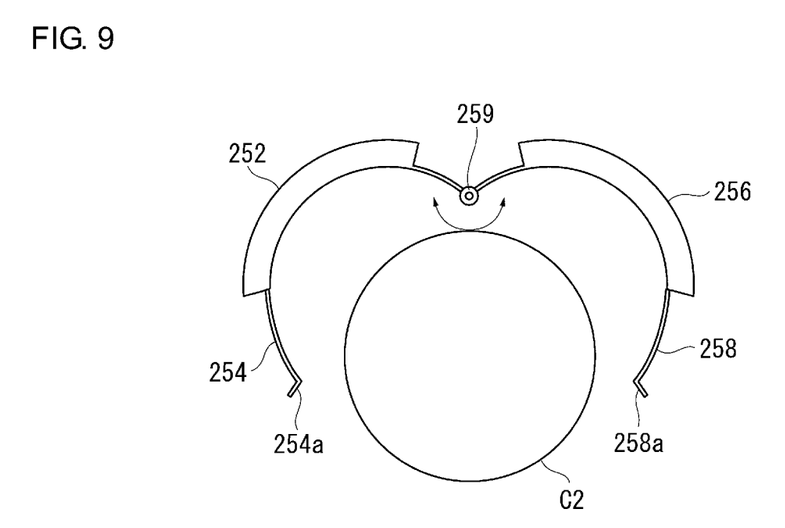
FIG. 9 is a view of an embodiment in which a first arc portion and a second arc portion are connected at a connection portion, as viewed in the axial direction.

For example, as shown in FIG. 9, a protection member 250 composed of a single member may be used. The protection member 250 includes a first arc portion 252 and a second arc portion 256 which are connected together by a connection portion 259 and cannot be separated from each other. The connection portion 259 is composed of, for example, a hinge or a flexible member formed of resin. The spacing between the first arc portion 252 and the second arc portion 256 in the radial direction can be expanded and contracted through rotation of opposite halves of the connection portion 259 in the radial direction.

By virtue of this, as in the case of the first embodiment, when viewed in the direction of the axial line O, the first arc portion 252 and the second arc portion 256 meet each other and can cover at least 90% (in total) of the entire circumference of the outer surface of the protection outer casing 190. Also, since the only requirement is to attach the protection member 250 by causing the first arc portion 252 and the second arc portion 256 to meet each other while rotating the opposite halves of the connection portion 259, it is unnecessary to forcedly expand a single arc portion. Consequently, the single protection member 250 can be easily and detachably fixed without deforming the protection member 250.

Notably, as in the case of the first embodiment, a fixation portion 254 is integrally connected to one end of the first arc portion 252 in the circumferential direction, and a fixation portion 258 is integrally connected to one end of the second arc portion 256 in the circumferential direction. Further, the fixation portions 254 and 258 have guide portions 254a and 258a, respectively, at their ends.

The other end of the first arc portion 252 in the circumferential direction and the other end of the second arc portion 256 in the circumferential direction are connected to each other by means of the connection portion 259.

Figure 10:
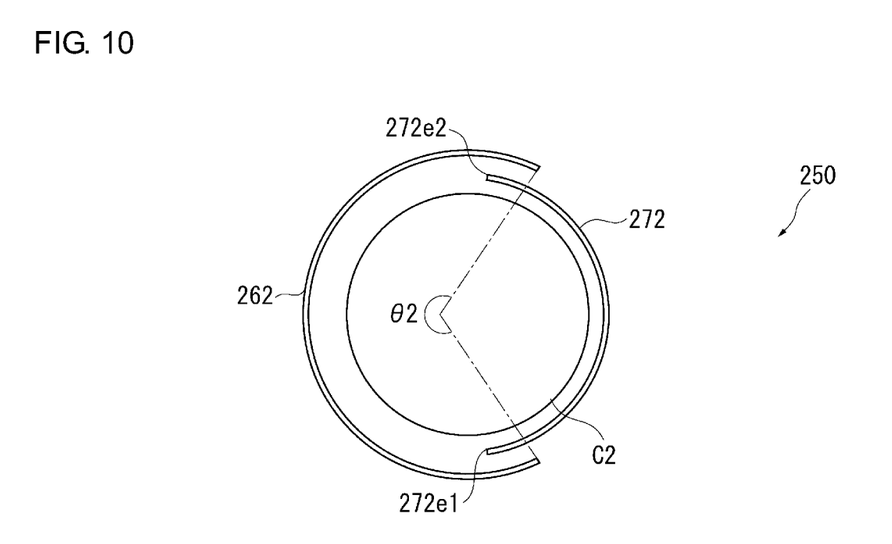
FIG. 10 is a view of an embodiment in which a first arc portion has a diameter greater than that of a second arc portion, as viewed in the axial direction.

Also, as shown in FIG. 10, a first arc portion 262 may have a dimeter greater than that of a second arc portion 272 and the center angle θ2 of the first arc portion 262 may be greater than 180 degrees. As in the case of the first embodiment, in a state in which the arc portions 262 and 272 have been attached to the protection outer casing 190, end portions 272e1 and 272e2 of the second arc portion 272 on opposite sides in the circumferential direction are covered by the first arc portion 262.

By virtue of this configuration, as in the case of the second embodiment, when the first arc portion 262 and the second arc portion 272 are caused to meet each other, the opposite ends of the first arc portion 262 do not interfere with opposite ends of the second arc portion 272. Therefore, the operation of attaching the first arc portion 262 and the second arc portion 272 becomes easy.

Also, since opposite ends of the first arc portion 262 overlap with the opposite ends of the second arc portion 272, the entire circumference (100%) of the outer surface of the outer surface member (the protection outer casing 190) can be covered without forming a gap. As a result, the effect of protecting the outer surface member can be obtained without fail.

The sensor element is not limited to the above-described plate-shaped element and may be a tubular element. Also, the positions and numbers of the crimped portions and the weld portion are not limited to the above-described positions and numbers.

Also, examples of the gas sensor include not only an oxygen sensor and a full-range gas sensor, but also an NOx sensor.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

The invention claimed is:

1. A gas sensor comprising:
a sensor element extending in an axial direction;
a metallic shell which surrounds a circumference of the sensor element and holds the sensor element;
a tubular outer surface member which is attached directly or indirectly to the metallic shell, constitutes an outer surface of the gas sensor, and extends toward a rear end side in relation to the metallic shell; and
a tubular protection member which is detachably fixed to a fixation region of an outer circumference of the outer surface member,
the gas sensor being characterized in that
the tubular protection member includes a first arc portion, a second arc portion, and a fixation portion which is brought into contact with and is fixed to the fixation region; and
when the tubular protection member fixed to the outer circumference of the outer surface member by fixing the fixation portion to the fixation region is viewed in the axial direction, the first arc portion and the second arc portion cover in total at least 90% of the entire circumference of the outer surface of the outer surface member,
wherein the tubular protection member is composed of two members which have the first arc portion and the second arc portion, respectively, and individual fixation portions connected to the first arc portion and the second arc portion, respectively, and the first arc portion and the second arc portion can be separated from each other.

2. The gas sensor as claimed in claim 1, wherein the first arc portion and the second arc portion of the tubular protection member are connected by means of a connection portion, and the spacing between the first arc portion and the second arc portion in a radial direction can be expanded and contracted by rotation of opposite halves of the connection portion in the radial direction.

3. The gas sensor as claimed in claim 1, wherein, when the tubular protection member fixed to the outer circumference of the outer surface member is viewed in the axial direction, the first arc portion and the second arc portion cover the entire circumference of the outer surface of the outer surface member.

4. The gas sensor as claimed in claim 1, wherein
the outer surface of the outer surface member has a diameter-reduced portion recessed inward in the radial direction and serving as the fixation region; and
the fixation portion is fitted onto the diameter-reduced portion, thereby being fixed to the diameter-reduced portion.

5. The gas sensor as claimed in claim 1, wherein the outer surface member has a ventilation hole for introducing outside air into a space inside the outer surface member;

an air-permeable filter is disposed on an inner surface of the outer surface member to close the ventilation hole; and the first arc portion and the second arc portion cover the ventilation hole from a radially outer side and form gaps for establishing communication between the ventilation hole and an outside atmosphere, the gaps being located at positions different from that of the ventilation hole in the axial direction.

6. The gas sensor as claimed in claim 1, wherein the total sum of a center angle of the first arc portion and a center angle of the second arc portion is greater than 360 degrees.

7. The gas sensor as claimed in claim 6, wherein a diameter of the first arc portion and a diameter of the second arc portion are the same;

one end portion of the first arc portion in a circumferential direction covers the outer surface of the outer surface member, and the other end portion of the first arc portion covers one end portion of the second arc portion in the circumferential direction; and the one end portion of the second arc portion in the circumferential direction covers the outer surface of the outer surface member, and the other end portion of the second arc portion covers the one end portion of the first arc portion in the circumferential direction.

8. The gas sensor as claimed in claim 6, wherein a diameter of the first arc portion is greater than a diameter of the second arc portion;

the first arc portion has a center angle greater than 180 degrees; and end portions of the second arc portion on opposite sides in the circumferential direction are covered by the first arc portion.

9. The gas sensor as claimed in claim 1, wherein the fixation portion has elasticity;

when viewed in the axial direction, the fixation portion has the shape of an arc having a center angle greater than 180 degrees and an opening;

the minimum spacing of the opening in the circumferential direction is smaller than the outer diameter of the fixation region; and the fixation portion has guide portions located at opposite ends of the opening, and the spacing between the guide portions in the circumferential direction expands from the minimum spacing.

10. A protection member for a gas sensor including a sensor element extending in an axial direction, a metallic shell surrounding a circumference of the sensor element and holding the sensor element, and a tubular outer surface member attached directly or indirectly to the metallic shell, constituting an outer surface of the sensor element, and extending toward a rear end side in relation to the metallic shell, the protection member being characterized in that the protection member is detachably fixed to a fixation region of an outer circumference of the outer surface member;

the protection member includes a first arc portion, a second arc portion, and a fixation portion which is brought into contact with and is fixed to the outer surface member; and when the protection member fixed to the outer circumference of the outer surface member by fixing the fixation portion to the outer surface member is viewed in the axial direction, the first arc portion and the second arc portion cover in total at least 90% of the entire circumference of the outer surface of the outer surface member, wherein the protection member is composed of two members which have the first arc portion and the second arc portion, respectively, and individual fixation portions connected to the first arc portion and the second arc portion, respectively, and the first arc portion and the second arc portion can be separated from each other.

* * * * *